United States Patent [19]

Showalter et al.

[11] Patent Number: 5,388,448

[45] Date of Patent: Feb. 14, 1995

[54] CONDUCTIVE PARTICLE DETECTOR

[75] Inventors: Stephen Showalter, Glenolden; James L. Horan, Morton, both of Pa.

[73] Assignee: Vickers, Incorporated, Maumee, Ohio

[21] Appl. No.: 105,146

[22] Filed: Aug. 12, 1993

[51] Int. Cl.⁶ .................................................. G01R 27/02
[52] U.S. Cl. ....................................... 73/61.71; 324/693
[58] Field of Search ........................... 73/61.71, 61.72; 324/693; 340/631

[56] References Cited

U.S. PATENT DOCUMENTS

| | | | |
|---|---|---|---|
| 2,716,165 | 8/1955 | Pfitzner | 340/631 X |
| 3,373,352 | 3/1968 | Huigens | 73/61.71 X |
| 3,686,926 | 8/1972 | Miller et al. | 73/61.72 |
| 3,878,103 | 4/1975 | Miller et al. | 340/631 X |
| 4,030,028 | 6/1977 | Allender | 324/693 X |
| 4,176,545 | 12/1979 | Oddo | 73/61.72 X |
| 4,657,671 | 4/1987 | Botstiber . | |
| 5,118,410 | 6/1992 | Rumberger | 340/631 X |
| 5,179,346 | 1/1993 | McGee et al. | 324/693 |

OTHER PUBLICATIONS

Tedeco Electromesh Indicating Screen brochure (one page, no date).

*Primary Examiner*—Thomas P. Noland
*Assistant Examiner*—Joseph W. Roskos
*Attorney, Agent, or Firm*—Barnes, Kisselle, Raisch, Choate, Whittemore & Hulbert

[57] ABSTRACT

An electrically conductive particle detector that includes a hollow spool or sleeve of insulating material having an open end, a sidewall and a circumferential array of elongated fluid passages that extend radially through the sidewall. A pair of internested helical conductors are mounted in corresponding helical grooves on the interior of the sleeve sidewall, with helical reaches of the conductors spaced from each other by the sleeve. Electrical circuitry is connected to the conductors for detecting impingement of a conductive particle that bridges adjacent reaches of the conductors in fluid that flows through the sleeve. A perforated strainer is carried by the sleeve spaced from the conductors for removing particles in the fluid that flows through the sleeve.

12 Claims, 3 Drawing Sheets

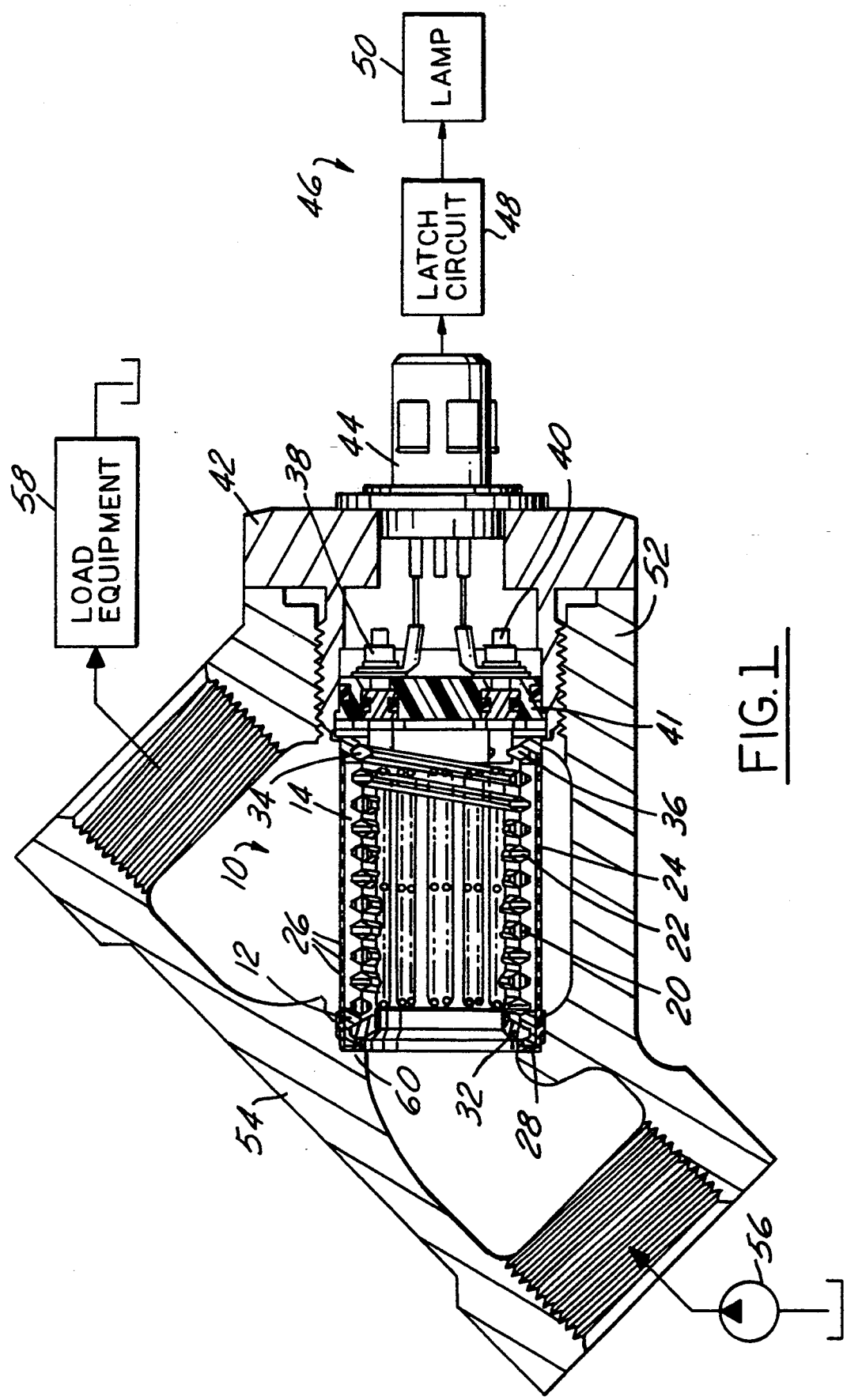

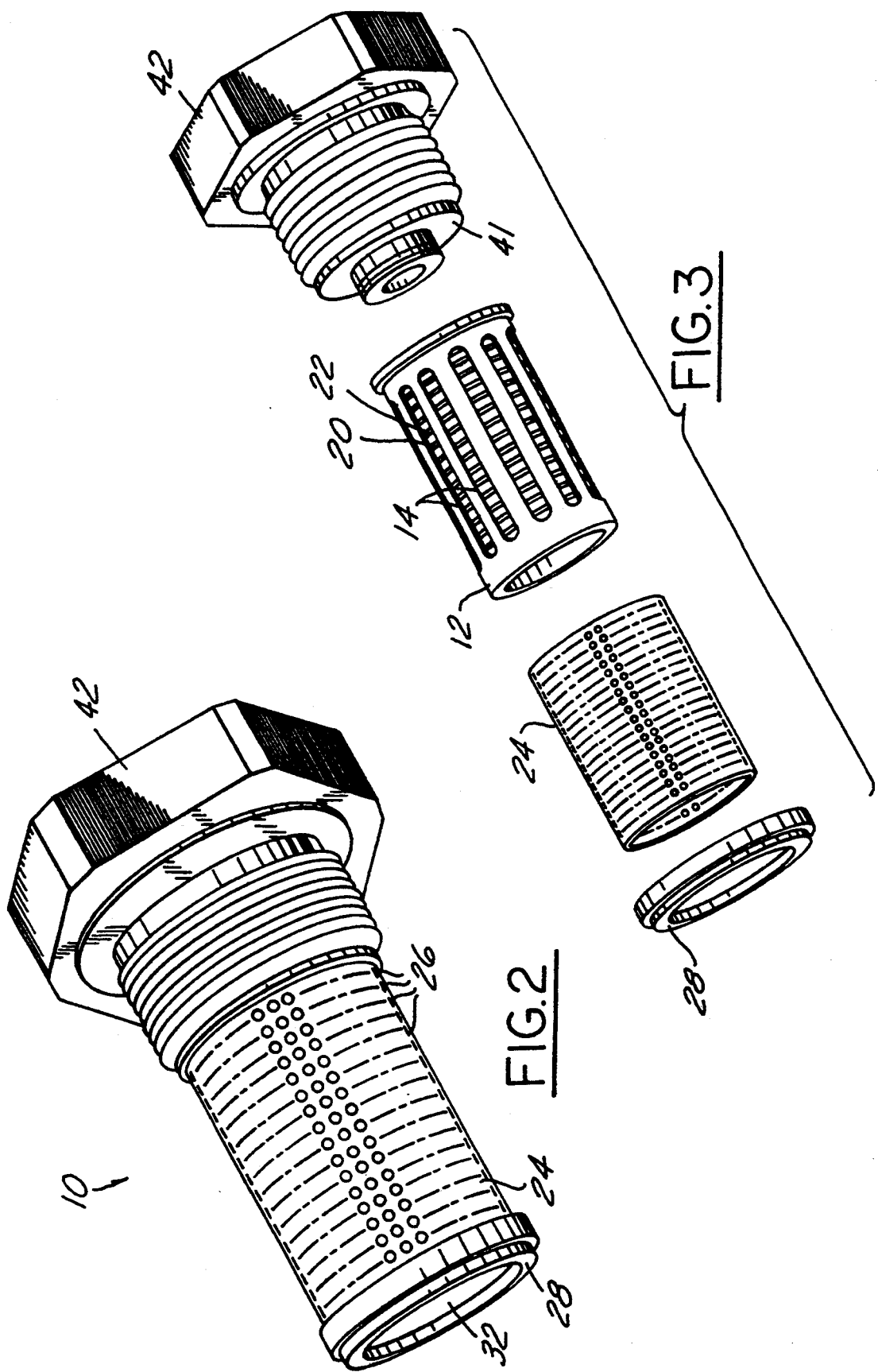

CONDUCTIVE PARTICLE DETECTOR

The present invention is directed to an improved device for detecting electrically conductive particles in fluid circulation systems, and to a method of constructing such a detector.

BACKGROUND AND OBJECTS OF THE INVENTION

In fluid circulation systems such as hydraulic, lubrication and cooling systems, it is desirable to provide facility for detecting presence of particles suspended in the fluid, which might indicate a need for maintenance or repair of the system. For example, in hydraulic transmission systems, it is desirable both to detect presence of metal particles or chips suspended in the fluid, and to remove such particles for preventing damage to the pump or transmission. Conventionally, particle detectors of the subject character are constructed of a mesh or screen woven from stainless steel and polyester filaments. The mesh is cut and formed to the desired shape, often cylindrical, and the ends of the conductive filaments are welded to each other at each end of the shape. The mesh is attached by epoxy or other bonding material to a structural frame, and electrical connection is made to the conductive filaments. When the structural frame is electrically conductive, phenolic or other suitable insulators must be interposed between the mesh and the frame. Conductive particles are detected when they bridge adjacent conductive filaments.

Although the wire mesh-type particle detectors described above have enjoyed commercial acceptance and success, improvements are desirable. In particular, the described particle detectors are difficult and expensive to manufacture, and are often not as robust as desirable for industrial and aircraft applications, for example. It is therefore a general object of the present invention to provide a particle detector of the described character that is inexpensive to manufacture, that is well suited for high-volume production, that is of robust character, and that provides reliable particle detection and filtering over an extended operating life. Another object of the present invention is to provide a method of constructing such a detector.

SUMMARY OF THE INVENTION

An electrically conductive particle detector in accordance with a presently preferred embodiment of the invention comprises a hollow spool or sleeve of insulating material having an open end, a sidewall and at least one fluid passage that extends radially through the sidewall. Two or more internested helical conductors are mounted in fixed position on the sleeve sidewall with helical reaches of the conductors spaced from each other. Electrical circuitry is connected to the conductors for detecting presence of a conductive particle that bridges adjacent reaches of the conductors in fluid that flows through the sleeve. A perforated strainer may be carried by the sleeve spaced from the conductors for removing particles in the fluid that flows through the sleeve.

In the preferred embodiment of the invention, the sleeve is formed with two internested helical grooves on the inner face of the sleeve sidewall, and the helical conductors are disposed in the respective grooves. In the preferred method of construction, the helical grooves are preformed in the sleeve wall, and the respective conductors are threaded into the preformed grooves. The pitches of the conductors and grooves are identical, but the conductors have a nominal diameter slightly greater than that of the grooves, so that the conductors are held in position in the sleeve grooves by torsional compressive forces without adhesive or other bonding means. Electrical terminals provide connection to the respective conductors without welding or similar operations. The resulting detector and strainer is both robust and inexpensive to manufacture.

BRIEF DESCRIPTION OF THE DRAWINGS

The invention, together with additional objects, features and advantages thereof, will be best understood from the following description, the appended claims and the accompanying drawings in which:

FIG. 1 is a schematic diagram of a fluid circulation system that includes a conductive particle detector in accordance with a presently preferred embodiment of the invention;

FIG. 2 is a perspective view of the particle detector illustrated in FIG. 1;

FIG. 3 is an exploded perspective view of the particle detector illustrated in FIGS. 1-2;

DETAILED DESCRIPTION OF PREFERRED EMBODIMENT

Figure 4:
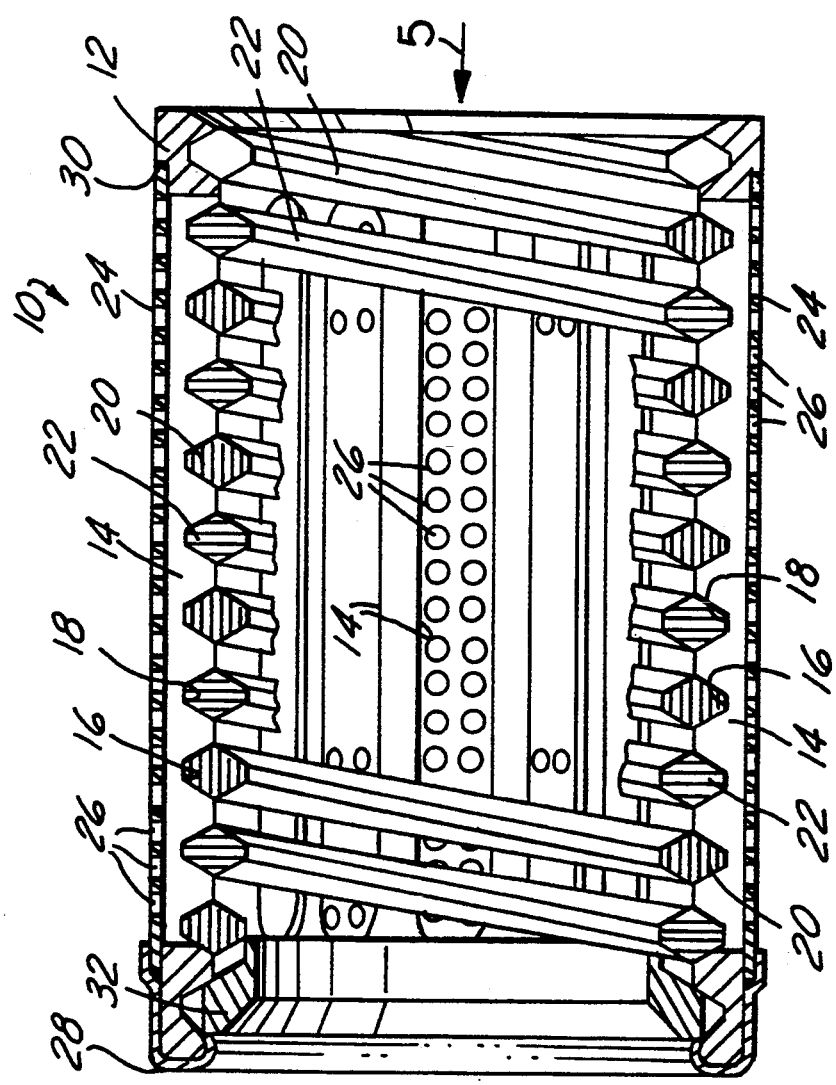
FIG. 4 is an elevational view that bisects a portion of the detector illustrated in FIGS. 1-3.

The drawings illustrate a particle detector 10 in accordance with a presently preferred embodiment of the invention as comprising a hollow cylindrical spool or sleeve 12 of uniform diameter and having an array of uniformly spaced elongated slots 14 that extend radially through the sidewall of the sleeve. A pair of internested non-intersecting spiral grooves or channels 16, 18 are formed on the inner face of sleeve 12 substantially throughout its length. A pair of internested electrical conductors 20, 22 are respectively disposed in the spiral grooves 16, 18, so that adjacent reaches of the conductors alternate between the conductors 16, 18 and are uniformly spaced from each other lengthwise of the sleeve as illustrated in FIG. 4. A strainer sleeve 24 having a multiplicity of perforations 26 is captured by a cap 28 that surrounds one open end of sleeve 12, and is held by the cap against a shoulder 30 on the opposing end of sleeve 12. An annular retainer 32 is captured by ring 28 within sleeve 12 against the ends of spiral conductors 20, 22.

Figure 5:
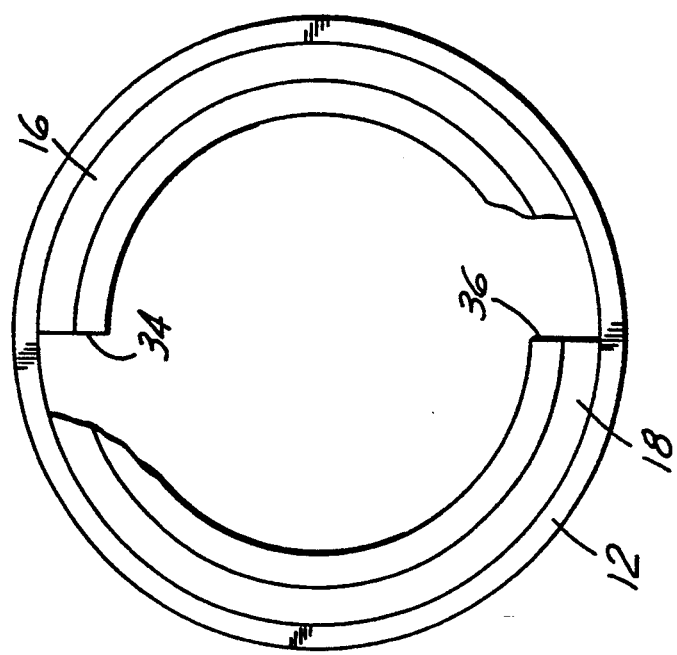
FIG. 5 is an end elevational view taken from the direction 5 in FIG. 4.

As shown in FIG. 5, spiral conductors 20, 22 have respective ends 34, 36 that are angularly offset from each other, preferably although not necessarily by an angle of 180°. A pair of screw terminals 38, 40 (FIG. 1) are carried by a plate 41 over the end of sleeve 12 adjacent to conductor ends 34, 36, and make electrical contact with the respective conductors 20, 22. A mounting nut 42 carries an electrical connector 44 that is coupled by suitable conductors to the respective terminals 38, 40 for connecting the terminals, and thereby connecting conductors 20, 22, to external particle detection circuitry 46. FIG. 1 illustrates typical detection circuitry 46 as including a latch circuit 48 responsive to momentary contact of a conductive particle bridging adjacent reaches of conductors 20, 22 for illuminating a lamp 50.

Detector 10 is mounted by external threads of nut 42 within an internally threaded passage 52 that branches at an angle from the main flow path of a fluid conduit or housing 54. An inlet end of housing 54 receives fluid under pressure from a pump schematically illustrated at 56, and the outlet end of the housing feeds the fluid to suitable load equipment 58 such as a transmission. Nut 42 holds the opposite open end of detector 10 against an annular seat 60 within housing 54, so that fluid flowing through the housing enters the open end of detector 10, and then passes between conductors 20, 22, through sleeve sidewall passages 14 and then through perforations 26 in strainer 24 to the fluid outlet. Any conductive particles carried by the fluid that bridge adjacent reaches of conductors 20, 22 energize latch circuit 48 and illuminate lamp 50. The size of the particles so detected depends upon the pitch of and spacing between adjacent conductor reaches and the width of sleeve passage slots 14. Perforated strainer 24 functions to filter particles of smaller size, and any larger particles that flow past conductors 20, 22.

In the preferred method of constructing detector 10, sleeve 12 is preformed in an injection molding operation or the like. Spiral grooves 16, 18 are formed during such molding operation (as are slots 14) at predetermined identical and uniform pitch and diameter. Spiral conductors 20, 22 are likewise preformed at the same uniform pitch as the sleeve grooves 16, 18, but at slightly greater diameter. Conductors 20, 22 are then threaded into the respective grooves 16, 18. Since the conductors initially possessed slightly larger diameter than the grooves, the conductors are held in place by torsional compressive forces applied from the sleeve to the conductors, and therefore do not require application of separate adhesives or the like. With the conductors so in place, retainer 32, strainer 24 and cap 28 are then assembled to the sleeve as shown in FIG. 4, and plate 41 with terminals 38, 40 are then also assembled to the sleeve as shown in FIG. 1. Sleeve 12 may also be injection molded around prepositioned conductors 20, 22, although such method of assembly is not currently preferred.

The preferred embodiment of the invention has been described hereinabove and illustrated in the drawings in conjunction with a single pair of conductors 20, 22 in a single pair of grooves 16, 18 on the inner face of sleeve 12. A multizone sensor can be constructed employing three or more internested conductors. In the same way, the conductors and grooves can be placed on the outer rather than the inner surface of the sleeve without departing from the invention in its broadest aspects.

We claim:

1. Apparatus for detecting electrically conductive particles in a fluid stream comprising:
   a sleeve of insulating material having an open end, a sidewall and at least one fluid passage through said sidewall,
   at least two internested helical conductors mounted on said sleeve sidewall in fixed position with helical reaches of said conductors spaced from each other, and
   means for electrical connection to said conductors for detecting a conductive particle bridging reaches of said conductors in fluid that flows through said open end and said at least one passage in said sleeve.

2. The apparatus set forth in claim 1 wherein said sleeve includes at least two internested helical grooves in one face of said sidewall, and wherein said helical conductors are disposed in respective ones of said grooves.

3. The apparatus set forth in claim 2 wherein said grooves are disposed in an internal face of said sidewall.

4. The apparatus set forth in claim 3 wherein said helical grooves are preformed in said sleeve at predetermined uniform diameter and pitch, and wherein said helical conductors are preformed apart from said sleeve at the same said predetermined uniform pitch but greater in diameter than said predetermined diameter, said spiral conductors being held in place within said sleeve by compressive forces on said conductors.

5. The apparatus set forth in claim 2 wherein said sleeve has a multiplicity of said fluid passages that extend radially through said sidewall.

6. The apparatus set forth in claim 5 wherein said multiplicity of fluid passages comprise an array of elongated slots uniformly spaced around said sleeve.

7. The apparatus set forth in claim 6 further comprising a perforated strainer carried by said sleeve for removing particles from fluid that flows through said sleeve.

8. In a fluid circulation system that includes means for feeding fluid under pressure to a load, apparatus for detecting conductive particles suspended in the fluid comprising:
   a hollow sleeve of electrical insulating material having an open end, a cylindrical sidewall, a plurality of fluid passages extending radially through said sidewall and at least two internested helical grooves on an internal face of said sidewall,
   at least two electrical conductors disposed in respective ones of said grooves,
   means for electrical connection to said conductors for detecting a conductive particle bridging adjacent reaches of said conductors, and
   means for positioning said sleeve in a fluid flow path such that fluid flows into said sleeve through said open end, between said conductors and then through said passages.

9. The apparatus set forth in claim 8 further comprising a perforated strainer carried by said sleeve for removing particles from fluid that flows through said sleeve.

10. The apparatus set forth in claim 9 wherein said means for positioning said sleeve comprises a section of fluid conduit having an inlet, an outlet and means forming a flow path connecting said inlet and outlet, an opening at an angle to said path, and means for removably mounting said sleeve in said path through said opening with said open end of said sleeve facing said inlet.

11. A method of making a particle detector comprising the steps of:
   (a) forming a hollow tubular sleeve having an open end, at lest one sidewall through passage, and at least two internested spiral non-intersecting grooves at predetermined uniform diameter and pitch,
   (b) forming at least two spiral conductors having the same said predetermined pitch but greater diameter than said grooves, and
   (c) threading said conductors into corresponding said grooves such that torsional compression on said conductors holds said conductors in place.

12. The method set forth in claim 11 wherein said step (a) is performed in a single injection molding operation.

* * * * *